(12) United States Patent
Boynton

(10) Patent No.: US 6,881,750 B2
(45) Date of Patent: Apr. 19, 2005

(54) POTASSIUM TAURATE BICARBONATE AND ASCORBATE

(75) Inventor: Herb Boynton, La Jolla, CA (US)

(73) Assignee: Nutrition Corp. of America, Ltd., La Jolla, CA (US)

( * ) Notice: Subject to any disclaimer, the term of this patent is extended or adjusted under 35 U.S.C. 154(b) by 0 days.

(21) Appl. No.: 10/756,205

(22) Filed: Jan. 13, 2004

(65) Prior Publication Data

US 2004/0176442 A1 Sep. 9, 2004

Related U.S. Application Data

(60) Provisional application No. 60/452,507, filed on Mar. 4, 2003.

(51) Int. Cl.$^7$ ........................ A61K 31/34; A61K 31/185
(52) U.S. Cl. ........................................ 514/474; 514/578
(58) Field of Search .................................. 514/474, 578

(56) References Cited

U.S. PATENT DOCUMENTS

| | | |
|---|---|---|
| 4,199,601 A | 4/1980 | Durlach |
| 5,434,276 A | 7/1995 | Walele et al. |
| 5,582,839 A | 12/1996 | McCarty |
| 5,651,813 A | 7/1997 | Santilli et al. |
| 5,723,496 A | 3/1998 | Nakada |
| 5,776,498 A | 7/1998 | McCarty |
| 5,776,504 A | 7/1998 | McCarty |
| 5,876,757 A | 3/1999 | McCarty |
| 5,985,017 A | 11/1999 | Bugner et al. |
| 6,099,869 A | 8/2000 | McCarty |
| 6,200,950 B1 | 3/2001 | Michalski et al. |
| 6,203,823 B1 | 3/2001 | McCarty |
| 6,294,520 B1 | 9/2001 | Naito |
| 6,337,094 B1 | 1/2002 | Guardiola et al. |

FOREIGN PATENT DOCUMENTS

| | | |
|---|---|---|
| EP | 0 778 021 A | 6/1997 |
| FR | 2 605 854 A | 5/1988 |

OTHER PUBLICATIONS

US 5,281,424, 1/1994, Morris et al. (withdrawn)
EAS High Performance RiboForce™ HP Product Description, (no date available).
Fennessy, F.M. et al.; "Taurine and Vitamin C Modify Monocyte and Endothelial Dysfunction In Young Smokers," Circulation 107 (3) 410 (2003).
Frassetto, L. et al.; "Diet, Evolution and Aging: The pathophysiologic effects of the post–agricultural inversion of the potassium–to–sodium and base–to–chloride ratios in the human diet," Eur J Nutr 40:200–213 (2001).
PBL Effervescent Creatine Plus—Orange Product Description.
Sacks, Frank M. et al.; "Effects on Blood Pressure of Reduced Dietary Sodium and the Dietary Approaches to Stop Hypertension (Dash) Diet," The New England Journal of Medicine, vol. 344, No. 1, Jan. 4, 2001, pp. 3–9.
Sternberg, Steve; "Dietary approach really does lower blood pressure'The lower the sodium, the steeper the drop,'" USA Today; Jan. 4, 2001, p. 9D.
Ultra Preventive® Forte–Chel tables, 150 tabs, Douglas Laboratories Product Description.
Yasutomi, C. et al.; "Anti–osteopenic effect of taurine: possible involvement of activated MEK ERK–Cbfa1 signaling," Nippon Yakurigaku Zasshi. Nov. 2002; 120(1):114P–115P (Abstract).
Sherry, A.D. et al., "Formation of Carbamates of Taurine and Other Amino Acids During Neutralization of Tissue Extracts with Potassium Carbonate/Bicarbonate," Journal of Magnetic Resonance, vol. 89, No. 2, 1990, pp. 391–398.
International Search Report for International Application No. PCT/US2004/006252 dated Jul. 22, 2004.

*Primary Examiner*—Raymond J. Henley, III
(74) *Attorney, Agent, or Firm*—Knobbe Martens Olson & Bear LLP

(57) ABSTRACT

Compositions comprising potassium taurate bicarbonate complexes and/or potassium taurate ascorbate complexes are useful as pharmaceutical compositions and as dietary ingredients in nutritional supplements, medical foods, and other foods. In preferred embodiments, potassium taurate bicarbonate and/or potassium taurate ascorbate complexes are the active ingredient in antihypertensive drug products that are intended to lower or prevent elevated blood pressure, or as dietary ingredients in dietary supplements, medical foods or other foods that are intended to supply a source of potassium, taurine, ascorbate, and/or bicarbonate, or that are intended to help maintain normal blood pressure levels and/or normal muscle mass. In preferred embodiments, potassium taurate bicarbonate complexes are prepared by intermixing potassium bicarbonate and taurine in aqueous solutions, and potassium taurate ascorbate complexes are prepared by intermixing potassium ascorbate and taurine in aqueous solutions.

50 Claims, 1 Drawing Sheet

Figure 1 – Effects of PTB (given in drinking water at 13.5 gr/L) vs tap water on the development of hypertension in conscious Dahl-SS (1.5 % KCl + 4% NaCl)
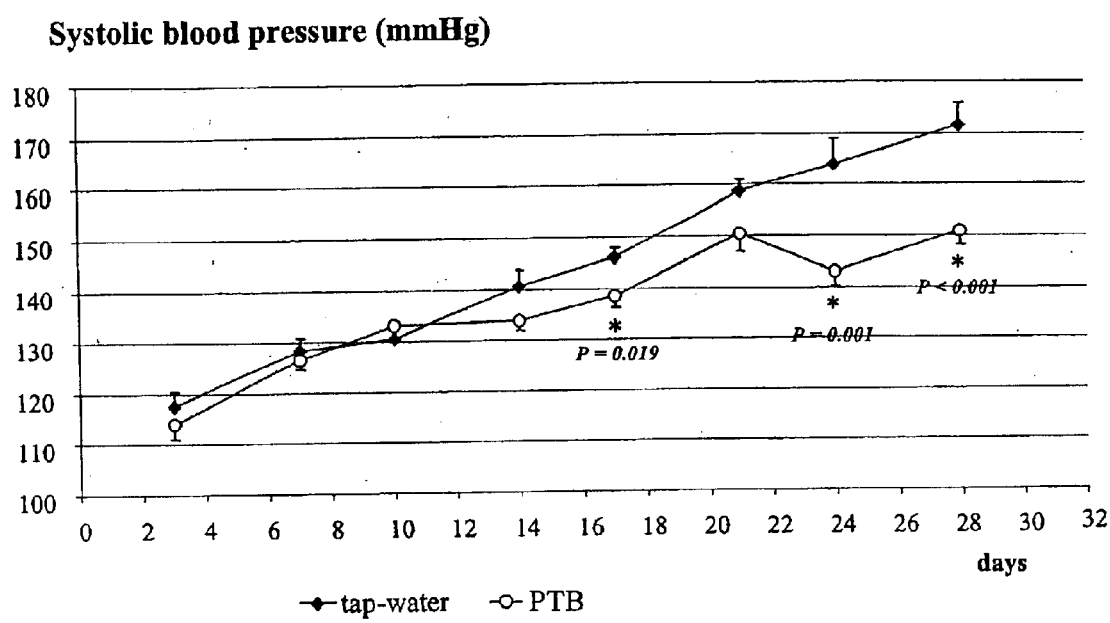
Results are expressed as mean ± S.E.M. for n=12 rats /group
(*) indicates a significant difference for P<0.05 (Student t test method) versus tap-water group.

POTASSIUM TAURATE BICARBONATE AND ASCORBATE

RELATED APPLICATION INFORMATION

This application claims priority to U.S. Provisional Application Ser. No. 60/452,507, filed Mar. 4, 2003, which is hereby incorporated by reference in its entirety.

BACKGROUND OF THE INVENTION

1. Field of the Invention

This invention relates to potassium taurate bicarbonate and potassium taurate ascorbate complexes and methods for making them, as well as methods for using such complexes as anti-hypertensive pharmaceutical agents, or as dietary ingredients in dietary supplements, medical foods or other food products.

2. Description of the Related Art

Primary hypertension, or high blood pressure, is a major risk factor for stroke, cardiovascular disease and death in the United States. Blood pressure levels are strongly and positively correlated with the habitual intake of sodium chloride. In populations with a sustained sodium chloride intake of 6 grams or more per day, blood pressure rises with age and hypertension is frequent, whereas in populations consuming less than 4.5 grams of sodium chloride per day, the age-related rise in blood pressure is slight or absent and the frequency of hypertension is uniformly low. See National Research Council, "Diet and Health: Implications for Reducing Chronic Disease Risk," National Academy Press, Washington D.C., 1989, which is hereby incorporated by reference in its entirety.

Epidemiological and animal studies indicate that the risk of stroke-related deaths is inversely related to potassium intake over the entire range of blood pressures, and the relationship appears to be dose dependent. The combination of a low-sodium, high-potassium intake is associated with the lowest blood pressure and the lowest frequency of stroke in individuals and populations. A substantial body of evidence in humans and animals indicates that dietary potassium exerts a beneficial effect on hypertension. This is partly because of its effect on lowering blood pressure and partly because of its separate, protective effect against vascular damage and stroke. Several studies have shown that supplemental potassium decreases the blood pressure of hypertensive patients. See H. Boynton et al., "The Salt Solution," Avery Penguin Putnam, Inc., New York, 2001; and Frank M. Sacks et al., "Effects on Blood Pressure of Reduced Dietary Sodium and the Dietary Approaches to Stop Hypertension (DASH) Diet," N. Engl. J. Med., Vol. 344 (1), pp. 3–9 (2001), both of which are hereby incorporated by reference in their entireties. However, despite the beneficial effects of potassium, nutritional potassium supplements are underutilized and not widely available. This may be because the U.S. Food and Drug Administration (FDA) currently limits the amount of potassium in a pill or tablet to 99 milligrams (mg), which is less than 3% of the Daily Value (3500 mg).

SUMMARY OF THE INVENTION

Preferred embodiments provide potassium taurate bicarbonate and potassium taurate ascorbate complexes in various forms, methods for making such compositions, methods for using such compositions as dietary ingredients in dietary supplements, medical foods or other food products, and as pharmaceutical compositions. Preferably, potassium taurate bicarbonate and potassium taurate ascorbate complexes are used as the active ingredient in antihypertensive drug products that are intended to lower or prevent elevated blood pressure, or as dietary ingredients in dietary supplements, medical foods or other foods that are intended to supply a source of potassium, taurine, bicarbonate, ascorbate, potassium taurate bicarbonate, and/or and potassium taurate ascorbate, or that are intended to help maintain normal blood pressure levels or otherwise to have a favorable impact on blood pressure.

A preferred embodiment provides a composition comprising a complex selected from the group consisting of potassium taurate bicarbonate complex and potassium taurate ascorbate complex, the composition preferably containing more potassium than sodium on a weight basis. Preferred compositions may be in various physical forms, preferably liquid but also solid. Preferably, a composition comprising a complex selected from the group consisting of potassium taurate bicarbonate complex and potassium taurate ascorbate complex is in the form of a pharmaceutical composition or dietary ingredient.

Another preferred embodiment provides a method for supplementing a diet, comprising administering a composition comprising a complex selected from the group consisting of potassium taurate bicarbonate complex and potassium taurate ascorbate complex to a mammal. Preferably, the composition is administered in an amount effective to provide the mammal with from about 100 mg to about 5,000 mg of potassium, and/or from about 100 mg to about 10,000 mg of taurine per day, and/or from about 25 mg to about 7,500 mg of bicarbonate per day, and/or from about 25 mg to about 7,500 mg of ascorbate per day. Preferably, the mammal is a human.

Another preferred embodiment provides a method for treating hypokalemia, comprising identifying a mammal suffering from hypokalemia, and administering a composition comprising a complex selected from the group consisting of potassium taurate bicarbonate complex and potassium taurate ascorbate complex to the mammal in an amount effective to treat the hypokalemia. Preferably, the mammal is a human.

Another preferred embodiment provides a method lowering elevated blood pressure, comprising identifying a mammal suffering from a hypertensive condition, and administering a composition comprising a complex selected from the group consisting of potassium taurate bicarbonate complex and potassium taurate ascorbate complex to the mammal in an amount effective to lower the elevated blood pressure. Preferably, the mammal is a human.

Another preferred embodiment provides a method for maintaining health, comprising administering a composition comprising a complex selected from the group consisting of potassium taurate bicarbonate complex and potassium taurate ascorbate complex to a mammal in an amount effective to maintain normal healthy blood pressure, normal healthy muscle mass, or both.

Another preferred embodiment provides a method for making a composition comprising a potassium taurate bicarbonate complex, comprising intermixing potassium bicarbonate, taurine and water.

Another preferred embodiment provides a method for making a composition comprising a potassium taurate ascorbate complex, comprising intermixing potassium ascorbate, taurine and water.

Another preferred embodiment provides a packaged liquid composition comprising about 300 to about 1,500 grams of water and about 100 mg to about 15 grams of a complex selected from the group consisting of potassium taurate bicarbonate complex and potassium taurate ascorbate complex. Preferably, the packaged liquid composition contains more potassium than sodium on a weight basis. Preferably, the packaged liquid composition comprises about 500 mg to about 2,000 mg of potassium.

Another preferred embodiment provides a solid mixture consisting essentially of potassium, ascorbic acid, optionally bicarbonate, and one or more ingredients selected from the group consisting of taurine and taurate. Another preferred embodiment provides a packaged product comprising such a solid mixture.

These and other embodiments are described in greater detail below.

BRIEF DESCRIPTION OF THE DRAWINGS

FIG. 1 is a plot illustrating the effects of PTB (given in drinking water) vs. tap water on the development of hypertension in Dahl salt-sensitive rats.

DETAILED DESCRIPTION OF THE PREFERRED EMBODIMENTS

Potassium taurate bicarbonate complexes ("PTB") provide three health-promoting dietary ingredients that are suboptimally supplied by most modern diets: potassium, bicarbonate, and taurine. Because of the over-inclusion of refined grains, sugars, oils, and fatty animal products in modern diets, as well as the under-inclusion of fruits and vegetables in many of these diets, dietary potassium intakes today are far lower than in the diets of our hunter-gatherer ancestors, who consumed no refined foods but likely had exceptionally high intakes of fruits and vegetables. According to USDA studies, about 82% of the U.S. population (2 years and older) consumes less than the Daily Value of potassium and about 52% consumes less than 70% of the Daily Value of potassium. Increased potassium intakes tend to lower blood pressure (particularly for people with high levels of sodium chloride in their diets), lower the risks of myocardial infarction and stroke, and preserve bone density by counteracting the tendency for sodium to induce renal calcium loss (calciuria).

Modern high-protein diets tend to be rich in sulfhydryl amino acids, which generate sulfuric acid when catabolized in the body, and thus tend to generate metabolic acidosis. Our bodies compensate by dissolving bone mineral, which generates phosphate buffer. This problem is exacerbated by the fact that many diets are relatively low in organic anions (such as those associated with potassium, calcium and magnesium in natural foods, especially fruits and vegetables) that can be metabolized in the body to yield bicarbonate ion, an effective buffer for metabolic acidosis that spares bone mineral. Chronic metabolic acidosis also induces muscle protein breakdown. Supplemental intake of bicarbonate slows bone turnover and renal calcium loss in postmenopausal women, thus reducing the risk of osteoporosis and fracture, slows or prevents age related loss of muscle mass, helps maintain normal bone density and muscle mass in healthy individuals, and helps to restore previously accrued muscle mass deficits.

Taurine is an amino acid having the chemical formula $H_2NCH_2CH_2SO_3H$. Taurate is the anionic form of taurine. It is understood that taurine and taurate may exist in equilibrium in solution. Although taurine contains a sulfonic acid group, it is not metabolized to yield sulfonic acid, and thus does not promote calciuria. The vascular effects of dietary taurine include: endothelial protective effects, platelet stabilization, anti-hypertensive, anti-inflammatory, anti-neuropathic, and anti-nephropathic benefits. Taurine is also an anti-oxidant nutrient.

Potassium taurate ascorbate complexes ("PTA") provide potassium, ascorbate and taurine. Ascorbate is the anionic form of ascorbic acid. Ascorbic acid is also known as vitamin C. It is understood that ascorbic acid and ascorbate may exist in equilibrium in solution. Ascorbic acid is important in forming collagen, a protein that gives structure to bones, cartilage, muscle, and blood vessels. Ascorbic acid also helps maintain capillaries, bones, and teeth and aids in the absorption of iron. The term "PTA/PTB" may used herein to refer to PTA, PTB, and/or mixtures thereof.

Products available commercially under the tradenames "Riboforce HP" and "PBL Effervescent Creatine Plus" contain potassium, taurine and bicarbonate. However, these products contain relatively small amounts of potassium and also contain significant amounts of sodium and creatine. For example, a single serving of the Riborforce HP product (recommended serving size according to product literature) contains more sodium (294 mg) than potassium (268 mg). Likewise, a single serving of the PBL Effervescent Creatine Plus product (recommended serving size according to product literature) also contains more sodium (300 mg) than potassium (150 mg). These products are apparently supplied for the purpose of increasing muscle, not lowering blood pressure. Tablets available commercially under the tradename "Ultra Preventative Forte-Chel" contain taurine and a potassium aspartate/ascorbate complex. However, the amount of potassium in each tablet is only 99 mg, less than 3% of the Daily Value (3500 mg), and the taurine is not in the form of taurate. These tablets are apparently supplied for general nutritional purposes, not for lowering blood pressure.

PTA/PTB complexes provides a convenient source of potassium, bicarbonate (for PTB), ascorbate (for PTA), and taurine for consumption by mammals, and particularly by humans. PTB is an ionic complex comprising potassium ion ($K^+$), bicarbonate and taurate in which the ratio of any particular component to any other particular component is in the range of about 10:1 to about 1:10, preferably in the range of about 2:1 to about 1:2, on a mole basis. For example, a preferred PTB is an ionic complex having approximately equimolar quantities of potassium ion, bicarbonate, and taurate, in which the molar ratio of each component to each other component is about 1:1. PTA is an ionic complex comprising potassium ion ($K^+$), ascorbate and taurate in which the ratio of any particular component to any other particular component is in the range of about 10:1 to about 1:10, preferably in the range of about 2:1 to about 1:2, on a mole basis. For example, a preferred PTA is an ionic complex having approximately equimolar quantities of potassium ion, ascorbate, and taurate, in which the molar ratio of each component to each other component is about 1:1.

Compositions comprising PTA/PTB may be in various forms, e.g., liquid form, solid form, or a mixture of liquid and solid. Those skilled in the art will understand that reference herein to a liquid form of PTA/PTB includes solutions in which the components are dissolved, as well as flowable multi-phase forms such as slurries and emulsions. Preferred PTA/PTB compositions comprise less sodium than potassium by weight. More preferably, the weight ratio of potassium to sodium in a PTA/PTB composition is about 2:1 or higher, even more preferably about 10:1 or higher. Because the FDA limits the amount of potassium in a pill or tablet intended for human consumption (current limit for commercial potassium supplements believed to be 99 mg), it is preferred that amounts in excess of the FDA limit be provided to the consumer in liquid form.

Liquid forms of PTA/PTB are preferably created by intermixing a potassium salt, an ascorbate salt (for PTA), a bicarbonate salt (for PTB), and taurine in an aqueous solution. It is understood that taurine may be employed in the form of a taurate salt, e.g., magnesium taurate. The aqueous solution contains water and may, optionally, contain one or more cosolvents such as ethanol. The relative amounts of potassium, bicarbonate (for PTB), ascorbate (for PTA), and taurine intermixed are preferably controlled so that the molar ratio of any particular component to any other particular component is in the range of about 10:1 to about 1:10, more preferably in the range of about 2:1 to about 1:2, most preferably about 1:1. The relative ratios may be adjusted by varying the relative amount of potassium salt (e.g., potassium bicarbonate, potassium ascorbate, potassium chloride), ascorbate salt (e.g., potassium ascorbate, calcium ascorbate, magnesium ascorbate), bicarbonate salt (e.g., potassium bicarbonate, calcium bicarbonate, magnesium bicarbonate), and taurine (e.g., magnesium taurate) added to the aqueous solution. This invention is not bound by theory, but it has been demonstrated that at least a portion of the potassium, ascorbate (for PTA), bicarbonate (for PTB) and taurine dissolve in the aqueous solution and react together to form a novel ionic potassium taurate bicarbonate and/or potassium taurate ascorbate complex, or mixture thereof.

In a preferred embodiment, potassium bicarbonate is used as a source of both potassium and bicarbonate. Intermixing is preferably conducted at a potassium bicarbonate to taurine molar ratio in the range of about 1:10 to about 10:1, more preferably in the range of about 2:1 to about 1:2. Intermixing in aqueous solution may be conducted at any convenient temperature, preferably in the range of about 0° C. to about 100° C. at atmospheric pressure. The taurine and/or potassium bicarbonate may be partly dissolved, e.g., in the form of a slurry. Complete dissolution of the constituents to form an aqueous solution may be achieved by heating and/or employing a sufficiently large amount of water. Such aqueous PTB solutions preferably have a pH in the range of about 7.0 to about 7.8. It has been found that the pH of a solution prepared by dissolving approximately equimolar amounts of taurine and potassium bicarbonate in water is about 7.4, thus indicating the formation of a PTB complex between potassium bicarbonate (solution pH about 8.4) and taurine (solution pH about 5.4).

In another preferred embodiment, potassium ascorbate is used as a source of both potassium and ascorbate. Potassium ascorbate from commercial sources typically contains a mixture of potassium bicarbonate and ascorbic acid in which the amount of potassium ranges from about 15% by weight to about 30% by weight. Intermixing of potassium ascorbate and taurine is preferably conducted at a potassium ascorbate to taurine molar ratio in the range of about 1:10 to about 10:1, more preferably in the range of about 2:1 to about 1:2. Intermixing in aqueous solution may be conducted at any convenient temperature, preferably in the range of about 0° C. to about 100° C. at atmospheric pressure. The taurine and/or potassium ascorbate may be partly dissolved, e.g., in the form of a slurry. Complete dissolution of the constituents to form an aqueous solution may be achieved by heating and/or employing a sufficiently large amount of water. Aqueous PTA solutions preferably have a pH in the range of about 4.5 to about 5.2, more preferably about 4.7 to about 5.0. In a preferred embodiment, potassium ascorbate and taurine in solid form (e.g., powder) are combined to form a solid mixture consisting essentially of potassium, ascorbic acid, optionally bicarbonate, and one or more additional ingredients selected from the group consisting of taurine and taurate. This solid mixture (preferably a powder containing less than about 3% water, by weight) is typically more stable than the corresponding aqueous solution, and may be more economical to ship and/or store. Thus, in a preferred embodiment, a solid mixture consisting essentially of potassium, ascorbic acid, optionally bicarbonate, and one or more additional ingredients selected from the group consisting of taurine and taurate, is supplied to the consumer as a packaged product, preferably with printed instructions directing the consumer to intermix the solid mixture with an aqueous liquid (such as water or fruit juice), to thereby form a PTA complex in the resulting solution. For example, the packaged product may comprise the solid mixture within a sealed enclosure of the general type used to supply powdered drink products to consumers. Preferably, the packaged product contains more than 99 mg of potassium, more preferably about 250 mg of potassium or more. PTA solutions prepared from solid mixtures may be stored for short periods of time, or consumed shortly after being prepared.

Compositions comprising PTA/PTB may be in various physical forms, e.g., liquids (including suspensions, emulsions, and slurries) and solids. The amount of PTA/PTB in such compositions is typically in the range of about 0.01% to about 100%, depending on the form of the product. For liquid forms, the amount of PTA/PTB in the composition is preferably in the range of about 0.01% to about 15%, more preferably about 0.1% to about 10%, by weight based on total weight. For solid forms, the amount of PTA/PTB in the composition is preferably about 25% or more, most preferably about 50% or more, by weight based on total weight. Preferably, the amount of sodium in the composition is less than the amount of potassium. More preferably, the weight ratio of potassium to sodium in the composition is about 2:1 or higher, even more preferably about 10:1 or higher. Solid forms of PTA/PTB may be obtained by evaporating the volatile components (e.g., water) from a liquid PTA/PTB composition to form an oily liquid, intermixing the oily liquid with an alcohol (e.g., ethanol) to precipitate solid PTA/PTB, then separating the solid PTA/PTB from the alcohol (e.g., by filtration).

In a preferred embodiment, PTA/PTB is provided to the consumer as a packaged liquid composition, e.g., as a fortified bottled water or sports drink product, comprising about 300 to about 1,500 grams of water and about 100 mg to about 15 grams of PTA/PTB. Preferably, the packaged liquid form of PTA/PTB contains about 250 mg to about 2500 mg of potassium, more preferably about 500 mg to about 2,000 mg of potassium; about 100 mg to about 10,000 mg of taurine, preferably about 300 mg to about 6,000 mg of taurine; about 25 mg to about 7,500 mg of ascorbate, more preferably about 50 mg to about 5,000 mg of ascorbate (for PTA), and about 25 mg to about 7,500 mg of bicarbonate, more preferably about 50 mg to about 5,000 mg of bicarbonate (for PTB). Preferably, the packaged liquid form of PTA/PTB contains less sodium than potassium by weight. More preferably, the packaged liquid form of PTA/PTB contains about 250 mg or less of sodium, even more preferably about 100 mg or less. The packaged liquid form of PTA/PTB may consist essentially of water and PTA/PTB, or may contain additional ingredients, e.g., vitamins, sweeteners, flavoring agents, coloring agents, preservatives, etc.

For oral administration, PTA/PTB compositions may be in various forms, e.g., a tablet, aqueous or oil suspension, dispersible powder or granule, emulsion, hard or soft capsule, syrup or elixir, and thus may comprise one or more carriers, e.g., edible carriers, pharmaceutically acceptable carriers, etc. Non-limiting examples of suitable carriers include inert diluents such as calcium carbonate, sodium carbonate, lactose, calcium phosphate or sodium phosphate; granulating and disintegrating agents, such as corn starch or alginic acid; binding agents such as starch, gelatin or acacia; and lubricating agents such as magnesium stearate, stearic acid or talc. PTA/PTB compositions intended for oral use may be prepared according to any method known in the art for the manufacture of food additives, nutritional supplements, and pharmaceutical compositions. Tablets may comprise PTA/PTB in admixture with edible and/or pharmaceutically acceptable carriers suitable for tablet manufacture. Tablets may be uncoated or coated by known techniques to delay disintegration and absorption in the gastrointestinal tract and thereby provide a sustained release and sustained action over a longer period of time. For example, a time delay material such as glyceryl monostearate or glyceryl distearate alone or with a wax may be employed. PTA/PTB compositions may contain one or more of the following agents: sweeteners, flavoring agents, coloring agents and preservatives.

PTA/PTB compositions for oral use may also be in the form of hard gelatin capsules in which the PTA/PTB is mixed with an inert solid carrier, for example calcium carbonate, calcium phosphate or kaolin, or as soft gelatin capsules in which the PTA/PTB is mixed with a liquid carrier such as water or an oil medium, e.g., peanut oil, liquid paraffin or olive oil. Aqueous PTA/PTB suspensions may contain the PTA/PTB in admixture with carriers suitable for the manufacture of aqueous suspensions. Such carriers include suspending agents, dispersing or wetting agents, one or more preservatives, one or more coloring agents, one or more flavoring agents and one or more sweetening agents such as sucrose or saccharin.

PTA/PTB compositions may also be in the form of oil-in-water emulsions. The oily phase may be a vegetable oil, such as olive oil or arachis oil, a mineral oil such as liquid paraffin, or a mixture thereof. Suitable emulsifying agents include naturally-occurring gums such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan monooleate. The emulsions may also contain sweetening and flavoring agents.

PTA/PTB compositions may be in the form of a dietary ingredient in a medical food, dietary supplement or other food product. PTA/PTB compositions may be used to supplement a diet by increasing the dietary intake of any one of potassium, taurine, ascorbate or bicarbonate; any two of the four (potassium and taurine, potassium and bicarbonate, potassium and ascorbate, taurine and ascorbate, ascorbate and bicarbonate, or taurine and bicarbonate); any three of the four (potassium, taurine, and bicarbonate; potassium, taurine and ascorbate; potassium, ascorbate and bicarbonate; or taurine, ascorbate, and bicarbonate) or all four (potassium, taurine, ascorbate and bicarbonate). For potassium, PTA/PTB compositions are preferably administered to mammals, more preferably humans, in an amount effective to provide the mammal with from about 100 milligrams to about 5,000 milligrams of potassium per day, more preferably about 500 milligrams to about 2,500 milligrams of potassium per day. PTA/PTB compositions may be advantageously administered in amounts effective to increase the potassium to sodium intake ratio for the mammalian recipient. Preferably, for a given sodium intake by the mammal, the PTA/PTB composition is administered in an amount effective to provide the mammal with a daily potassium intake that is greater than the daily sodium intake, more preferably at least about double the daily sodium intake. Thus, the medical food, dietary supplement or other food product preferably contains more potassium than sodium on a weight basis. More preferably, the weight ratio of potassium to sodium in the medical food, dietary supplement or other food product is about 2:1 or higher, even more preferably about 10:1 or higher.

For taurine, PTA/PTB compositions are preferably administered to mammals, more preferably humans, in an amount effective to provide the mammal with from about 100 milligrams to about 10,000 milligrams of taurine per day, more preferably about 300 milligrams to about 6,000 milligrams of taurine per day. For bicarbonate, PTB compositions are preferably administered to mammals, more preferably humans, in an amount effective to provide the mammal with from about 25 milligrams to about 7,500 milligrams of bicarbonate per day, more preferably about 50 milligrams to about 5,000 milligrams of bicarbonate per day. For ascorbate, PTA compositions are preferably administered to mammals, more preferably humans, in an amount effective to provide the mammal with from about 25 milligrams to about 7,500 milligrams of ascorbate per day, more preferably about 50 milligrams to about 5,000 milligrams of ascorbate per day.

In a preferred embodiment, the PTA/PTB composition is administered in the form of dietary ingredient in a medical food, dietary supplement or other food product to mammals having normal healthy blood pressures, and the amount of PTA/PTB composition administered is effective to maintain normal blood pressure in such mammals as they age. In another preferred embodiment, the PTA/PTB composition is administered in the form of dietary ingredient in a medical food, dietary supplement or other food product to mammals having normal healthy muscle mass, and the amount of PTA/PTB composition administered is effective to maintain normal muscle mass in such mammals as they age. Even more preferably, both normal blood pressure and normal muscle mass are maintained. The amounts of PTA/PTB effective for such purposes may be determined by routine experimentation. Administration of PTA/PTB may be self-administration or under the supervision of a medical professional. Preferably, administration of PTA/PTB further comprises controlling sodium intake so as not to exceed potassium intake on a weight basis. Preferably, potassium intake is at least about twice the sodium intake on a weight basis.

PTA/PTB compositions in the form of dietary ingredients in medical foods, dietary supplements or other food products are administered to the mammal orally, typically in an amount in the range of about 100 milligrams to about 20 grams daily. Amounts effective to maintain normal healthy blood pressure and/or muscle mass may be determined by those skilled in the art by routine experimentation or by such methods as clinical trials. Dietary intake levels may be adjusted in individual cases as required to maintain overall good health. In a preferred embodiment, the PTA/PTB is formulated into a nutritional supplement of the type generally sold in health food stores and suitable for oral administration as described above. In other preferred embodiments, PTA/PTB is provided to the consumer as a ingredient in food, e.g., breakfast cereal, fortified bottled water, flavored drink product, etc. The amount of PTA/PTB in the food is preferably adjusted so that consumption of the food in ordinary amounts provides the consumer with from about 500 milligrams to about 5,000 milligrams of potassium.

PTA/PTB compositions may also be in the form of a pharmaceutical composition used to diagnose, cure, mitigate, treat or prevent a disease, condition or disorder. For example, such compositions may be used as therapeutic agents to treat mammals, preferably humans, suffering from hypokalemia (low potassium) and/or from various hypertensive conditions, including hypertensive heart disease, hypertensive hemorrhage, hypertensive retinopathy, and primary hypertension. Primary hypertension is characterized by high blood pressure (systolic blood pressure consistently higher than 140, or diastolic blood pressure consistently over 90). Methods for treating mammals suffering from hypertensive conditions are preferably practiced by first identifying an individual suffering from a hypertensive condition or conditions. Methods for diagnosing such conditions are known to those skilled in the medical arts. Treatment of the identified individual is preferably conducted by administering a PTA/PTB composition to the individual in an amount effective to treat the hypertensive condition.

The amount of PTA/PTB composition administered as a pharmaceutical composition is typically in the range of about 100 milligrams to about 20 grams daily. Therapeutically effective amounts can be determined by those skilled in the art by such methods as clinical trials. Dosages may be adjusted in individual cases as required to alleviate the condition, e.g., hypertensive condition, to the desired degree. Sustained release dosages and infusions are specifically contemplated. PTA/PTB compositions can be administered by any appropriate route for systemic, local or topical delivery, for example, orally, parenterally, intravenously, intradermally, subcutaneously, buccally, intranasally, by inhalation, or topically, in liquid or solid form. Methods of administering the PTA/PTB compositions described herein may be by specific dose or by controlled release vehicles. The PTA/PTB composition may be administered at once, or may be divided into a number of smaller doses to be administered at varying intervals of time. It is to be further understood that for any particular subject, specific dosage regimens should be adjusted over time according to the individual need and the professional judgment of the person administering or supervising the administration of the compound, and that the dosage ranges set forth herein are exemplary only and are not intended to limit the scope or practice of the claimed methods.

Non-human mammals may also benefit from increased potassium, taurine and/or bicarbonate intake, and thus PTA/PTB compositions may be used as veterinary drugs or as veterinary dietary ingredients in veterinary supplements or in veterinary foods. For example, taurine is an essential amino acid for cats. PTA/PTB is preferably provided to cats in an amount that provides the cat with from about 400 milligrams to about 4,000 milligrams of taurine per kilogram of food ingested by the cat. Hypokalemia in cats has been associated with depression, inactivity, poor haircoat, mild anemia, and poor kidney function. To treat or prevent hypokalemia, PTA/PTB is preferably provided to cats in an amount that provides the cat with from about 500 milligrams to about 1,500 milligrams of potassium per kilogram of food ingested by the cat. Amounts of PTA/PTB effective to maintain health or treat various conditions in other species may be determined by routine experimentation.

EXAMPLE 1

An aqueous solution having a pH of about 8.4 was prepared by dissolving 500.6 milligrams (5 millimoles) of potassium bicarbonate ($KHCO_3$) in 25 milliliters (mL) of water with stirring. To this solution was added 625.5 milligrams (5 millimoles) taurine with stirring. The pH of the resulting aqueous solution was 7.4, indicating formation of potassium taurate bicarbonate complex.

EXAMPLE 2

A aqueous solution containing 10.0 grams (0.1 mole) potassium bicarbonate and 12.5 grams taurine (0.1 mole) in 50 milliliters of water was evaporated under reduced pressure. The oily residue was treated with 100 milliliters of ethanol and allowed to sit overnight to form a precipitate. The precipitate was collected by filtration, washed with ethanol and dried under reduced pressure to yield 21 grams of solid potassium taurate bicarbonate.

EXAMPLE 3

An experimental study was undertaken to assess the effect on blood pressure of oral PTB given in drinking water to Dahl salt-sensitive rats, which are known to experience an increase in blood pressure upon administration of salt. In this study, salt was administered in the diet to two groups of rats, a placebo group that received salt but not PTB and an active group that received both salt and PTB in drinking water. The results summarized in Table 1 and plotted in FIG. 1 show that PTB significantly blunted the expected rise in systolic blood pressure in the active group by an average of 21 mm Hg by the end of the 28-day study.

The study was conducted as follows: Twenty-four Dahl salt-sensitive male rats were fed regular rat chow containing 0.24% (w/w) sodium chloride for an acclimatization period. The rats were then switched to a high salt diet (4% NaCl and 1.5% KCl) and were randomly divided into two groups of twelve rats each—an active group supplied with drinking water containing 13.5 grams/liter PTB (prepared as described in Example 2, and a placebo group receiving ordinary drinking water. Food and water were available ad libitum to both groups over the 28-day course of the study. The systolic blood pressure of each rat was determined twice a week over the course of the study by the tail-cuff plethysmography method. Each recorded blood pressure was the average of 3–5 individual readings.

The systolic blood pressure results are summarized in Table 1 and plotted in FIG. 1. Systolic blood pressure rose progressively after high-salt intake in the placebo group, reaching 172±4 mm Hg at day 28. PTB treatment given in drinking water at 13.5 grams/liter significantly slowed the rise in blood pressure at day 17 and between days 24 and 28 (138±2, 143±3 and 151±3 in treated rats versus 146±2, 164±5 and 172±4 in untreated rats, respectively; P=0.019 for day 17, P=0.001 for day 24 and P=<0.001 for day 28).

TABLE 1

Average systolic blood pressure (mm Hg) in Dahl salt-sensitive rats after administration of tap water (placebo, control) or PTB (active) over course of 28 days

| Group | Days after administration | | | | | | | |
|---|---|---|---|---|---|---|---|---|
| | 3 | 7 | 10 | 14 | 17 | 21 | 24 | 28 |
| Placebo | 118 | 129 | 130 | 141 | 146 | 159 | 164 | 172 |
| Active | 114 | 126 | 133 | 134 | 138 | 150 | 143 | 151 |

EXAMPLE 4

About 6.0 grams of a commercial sample of potassium ascorbate in dry form (about 28% potassium) was blended with about 5.4 grams of dry taurine and ground to form a solid mixture in the form of a fine powder. About one gram of the solid mixture was dissolved in about 50 mL of water to form an aqueous solution containing a potassium taurate ascorbate complex. The solution had a pH of about 5 and a pleasant taste.

It will be appreciated by those skilled in the art that various omissions, additions and modifications may be made to the compositions and methods described above without departing from the scope of the invention, and all such modifications and changes are intended to fall within the scope of the invention, as defined by the following claims.

What is claimed is:

1. A composition comprising a complex selected from the group consisting of potassium taurate bicarbonate complex and potassium taurate ascorbate complex, and optionally sodium, the composition containing more potassium than sodium on a weight basis.

2. The composition of claim 1 in which the complex is potassium taurate bicarbonate complex.

3. The composition of claim 1 in which the complex is potassium taurate ascorbate complex.

4. The composition of claim 1 in which the complex comprises a mixture of potassium taurate bicarbonate complex and potassium taurate ascorbate complex.

5. The composition of claim 1 in solid form.

6. The composition of claim 1 in liquid form.

7. The composition of claim 1 having a potassium:taurine molar ratio in the range of about 1:10 to about 10:1.

8. The composition of claim 1 having a potassium:taurine molar ratio in the range of about 1:2 to about 2:1.

9. The composition of claim 1 further comprising an edible carrier.

10. The composition of claim 9 in which the complex comprises at least about 25%, by weight, of the composition.

11. The composition of claim 9 in which the complex comprises at least about 50%, by weight, of the composition.

12. The composition of claim 1 in the form of a pharmaceutical composition.

13. The composition of claim 1 in the form of a dietary ingredient.

14. The composition of claim 13 in the form of a medical food.

15. The composition of claim 13 in the form of a dietary supplement.

16. The composition of claim 13, further comprising food.

17. A method for supplementing a diet, comprising administering the composition of claim 1 to a mammal.

18. The method of claim 17, comprising administering the composition of claim 1 to the mammal in an amount effective to provide the mammal with from about 100 milligrams to about 5,000 milligrams of potassium per day.

19. The method of claim 17, comprising administering the composition of claim 1 to the mammal in an amount effective to provide the mammal with from about 100 milligrams to about 10,000 milligrams of taurine per day.

20. The method of claim 17 in which the complex is potassium taurate bicarbonate complex, comprising administering the composition of claim 1 to the mammal in an amount effective to provide the mammal with from about 25 milligrams to about 7,500 milligrams of bicarbonate per day.

21. The method of claim 17 in which the complex is potassium taurate ascorbate complex, comprising administering the composition of claim 1 to the mammal in an amount effective to provide the mammal with from about 25 milligrams to about 7,500 milligrams of ascorbate per day.

22. The method of claim 17 in which the mammal is a cat.

23. The method of claim 17 in which the mammal is a human.

24. The method of claim 23 in which the human has a daily sodium intake, comprising administering the composition of claim 1 to the human in an amount effective to provide the human with a daily potassium intake that is greater than the daily sodium intake.

25. The method of claim 24 comprising administering the composition of claim 1 to the human in an amount effective to provide the human with a daily potassium intake that is at least about double the daily sodium intake.

26. A method for treating hypokalemia, comprising
identifying a mammal suffering from hypokalemia; and
administering the composition of claim 1 to the mammal in an amount effective to treat the hypokalemia.

27. The method of claim 26 in which the mammal is a human.

28. The method of claim 26 in which the amount effective to treat the hypokalemia is an amount effective to provide the mammal with from about 100 milligrams to about 5,000 milligrams of potassium per day.

29. A method for treating a hypertensive condition, comprising
identifying a mammal suffering from a hypertensive condition; and
administering the composition of claim 1 to the mammal in an amount effective to treat the hypertensive condition.

30. The method of claim 29 in which the mammal is a human.

31. The method of claim 30 in which the amount effective to treat the hypertensive condition is an amount effective to provide the human with from about 100 milligrams to about 5,000 milligrams of potassium per day.

32. A method for maintaining normal healthy blood pressure, normal healthy muscle mass, or both, comprising administering the composition of claim 1 to a mammal in an amount effective to maintain normal healthy blood pressure, normal healthy muscle mass, or both.

33. A method for making the composition of claim 1 in which the complex is potassium taurate bicarbonate complex, comprising intermixing potassium bicarbonate, taurine and water.

34. The method of claim 33 in which the intermixing is conducted at a molar ratio of the potassium bicarbonate to the taurine in the range of about 1:10 to about 10:1.

35. The method of claim 33 in which the intermixing is conducted at a molar ratio of the potassium bicarbonate to the taurine in the range of about 1:2 to about 2:1.

36. The method of claim 33, further comprising evaporating the water to produce a solid potassium taurate bicarbonate complex.

37. The method of claim 33 in which the intermixing produces an aqueous solution having a pH in the range of about 7.0 to about 7.8.

38. A method for making the composition of claim 1 in which the complex is potassium taurate ascorbate complex, comprising intermixing potassium ascorbate, taurine and water.

39. The method of claim 38 in which the intermixing is conducted at a molar ratio of the potassium ascorbate to the taurine in the range of about 1:10 to about 10:1.

40. The method of claim 38 in which the intermixing is conducted at a molar ratio of the potassium ascorbate to the taurine in the range of about 1:2 to about 2:1.

41. The method of claim 38, further comprising evaporating the water to produce a solid potassium taurate ascorbate complex.

42. A packaged liquid composition comprising about 300 to about 1,500 grams of water and about 100 mg to about 15 grams of a complex selected from the group consisting of potassium taurate bicarbonate complex and potassium taurate ascorbate complex; and optionally sodium.

43. The packaged liquid composition of claim 42 in which the complex is potassium taurate bicarbonate complex.

44. The packaged liquid composition of claim 42 in which the complex is potassium taurate ascorbate complex.

45. The packaged liquid composition of claim 42 containing more potassium than sodium on a weight basis.

46. The packaged liquid composition of claim 42 comprising about 250 mg to about 2500 mg of potassium.

47. The packaged liquid composition of claim 42 comprising about 500 mg to about 2,000 mg of potassium.

48. The packaged liquid composition of claim 46 comprising about 100 mg to about 10,000 mg of taurine.

49. The packaged liquid composition of claim 46 comprising about 25 mg to about 7,500 mg of bicarbonate.

50. A packaged liquid composition consisting essentially of water and a complex selected from the group consisting of potassium taurate bicarbonate complex and potassium taurate ascorbate complex.

* * * * *

UNITED STATES PATENT AND TRADEMARK OFFICE
CERTIFICATE OF CORRECTION

PATENT NO. : 6,881,750 B2
DATED : April 19, 2005
INVENTOR(S) : Boynton

It is certified that error appears in the above-identified patent and that said Letters Patent is hereby corrected as shown below:

Column 11,
Line 65, delete "amounteffective" and insert -- amount effective --.

Signed and Sealed this

Seventh Day of February, 2006

JON W. DUDAS
*Director of the United States Patent and Trademark Office*